United States Patent [19]

Berg et al.

[11] Patent Number: 4,566,948
[45] Date of Patent: * Jan. 28, 1986

[54] SEPARATION OF ISOPROPYL ETHER FROM ISOPROPANOL AND WATER BY EXTRACTIVE DISTILLATION

[76] Inventors: Lloyd Berg, 1314 S. 3rd. Ave.; An-I Yeh, 700 S. 12th Ave., both of Bozeman, Mont. 59715

[*] Notice: The portion of the term of this patent subsequent to Jul. 10, 2001 has been disclaimed.

[21] Appl. No.: 684,367

[22] Filed: Dec. 20, 1984

[51] Int. Cl.$^4$ ............................................. B01D 3/40
[52] U.S. Cl. ........................................ 203/51; 203/56; 203/57; 203/58; 203/60; 203/63; 203/64; 203/14; 568/699
[58] Field of Search ................. 203/14, 51, 52, 56, 203/57, 58, 60, 63, 64; 568/699, 896

[56] References Cited

U.S. PATENT DOCUMENTS

| | | | |
|---|---|---|---|
| 2,085,546 | 6/1937 | Roelfsema | 203/57 |
| 2,461,048 | 2/1949 | Frejacques | 203/18 |
| 2,481,211 | 9/1949 | Fuqua | 203/63 |
| 2,570,205 | 10/1951 | Carlson et al. | 568/913 |
| 2,591,672 | 4/1952 | Catterall | 203/18 |
| 2,791,615 | 5/1957 | Nommensen | 568/699 |
| 4,459,178 | 7/1984 | Berg et al. | 203/56 |
| 4,510,022 | 4/1985 | Berg et al. | 203/56 |

FOREIGN PATENT DOCUMENTS 0556048  4/1958  Canada .............................. 568/913

Primary Examiner—S. Leon Bashore
Assistant Examiner—Virginia Manoharan

[57] ABSTRACT

Isopropyl ether cannot be completely removed from isopropyl ether-isopropanol-water mixtures by distillation because of the presence of the minimum ternary azeotrope. Isopropyl ether can be readily removed from mixtures containing it, isopropanol and water by using extractive distillation in which the extractive distillation agent is dimethylsulfoxide with or without a mixture of higher boiling oxygenated and/or nitrogenous organic compounds. Typical examples are dimethylsulfoxide; dimethylsulfoxide and ethylene glycol; dimethylsulfoxide, dimethylformamide and 1,4-butanediol.

2 Claims, No Drawings

SEPARATION OF ISOPROPYL ETHER FROM ISOPROPANOL AND WATER BY EXTRACTIVE DISTILLATION

FIELD OF THE INVENTION

This invention relates to a method for separating isopropyl ether from isopropanol using certain higher boiling liquids as the extractive agent in extractive distillation.

DESCRIPTION OF PRIOR ART

Extractive distillation is the method of separating close boiling compounds or azeotropes by carrying out the distillation in a multiplate rectification column in the presence of an added liquid or liquid mixture, said liquid(s) having a boiling point higher than the compounds being separated. The extractive agent is introduced near the top of the column and flows downward until it reaches the stillpot or reboiler. Its presence on each plate of the rectification column alters the relative volatility of the close boiling compounds in a direction to make the separation on each plate greater and thus requires either fewer plates to effect the same separation or make possible a greater degree of separation with the same number of plates. When the compounds to be separated normally form an azeotrope, the proper agents will cause them to boil separately during extractive distillation and thus make possible a separation in a rectification column that cannot be done at all when no agent is present. The extractive agent should boil higher than any of the close boiling liquids being separated and not form minimum azeotropes with them. Usually the extractive agent is introduced a few plates from the top of the column to insure that none of the extractive agent is carried over with the component of highest vapor pressure. This usually requires that the extractive agent boil twenty Centigrade degrees or more higher than the lowest boiling component.

At the bottom of a continuous column, the less volatile components of the close boiling mixtures and the extractive agent are continuously removed from the column. The usual methods of separation of these two components are the use of another rectification column, cooling and phase separation, or solvent extraction.

The most common method of manufacturing isopropanol is by the hydration of propylene using sulfuric acid as the catalyst. However before the isopropanol can be removed from the reaction mixture, some of it reacts with the sulfuric acid to form isopropyl ether. Thus isopropanol made by this method invariably contains some isopropyl ether as an impurity. Normally a mixture of several solvents are separated and recovered by fractionation in a multiplate rectification column and the ease of separation depends upon the difference in boiling points of the compounds to be separated. However isopropanol, isopropyl ether and water form three binary azeotropes and one ternary azeotrope as shown in Table I. Thus any mixture containing these three compounds subjected to rectification will produce an overhead product boiling at 61.6° C. and containing 4.7% water, 7.3% isopropanol and 88% isopropyl ether.

TABLE I

| Azeotropes of Isopropyl Ether, Isopropanol and Water. | | | | |
|---|---|---|---|---|
| Compounds | B.P., °C. | Azeotrope Composition, Wt. % | | |
| Water | 100 | | | |
| Isopropanol | 82.5 | | | |
| Isopropyl ether | 69.0 | | | |
| Water-Isopropanol | 80.3 | 12.6 | 87.4 | |
| Isopropanol-Isopropyl ether | 66.2 | 16.3 | 83.7 | |
| Water-Isopropyl ether | 62.2 | 4.5 | 95.5 | |
| Water-Isopropanol-Isopropyl ether | 61.6 | 4.7 | 7.3 | 88.0 |

Extractive distillation would be an attractive method of effecting the separation of isopropyl ether from isopropanol and water if agents can be found that (1) will break the isopropyl ether-isopropanol-water azeotrope and (2) are easy to recover from the isopropanol and water, that is, form no azeotrope with isopropanol and boil sufficiently above isopropanol to make the separation by rectification possible with only a few theoretical plates.

Extractive distillation typically requires the addition of an equal amount to twice as much extractive agent as the isopropyl ether-isopropanol-water on each plate of the rectification column. The extractive agent should be heated to about the same temperature as the plate into which it is introduced. Thus extractive distillation imposes an additional heat requirement on the column as well as somewhat larger plates. However this is less than the increase occasioned by the additional agents required in azeotropic distillation. Another consideration in the selection of the extractive distillation agent is its recovery from the bottoms product. The usual method is rectification in another column. In order to keep the cost of this operation to a minimum, an appreciable boiling point difference between the compound being separated and the extractive agent is desirable. It is also desirable that the extractive agent be miscible with isopropanol otherwise it will form a two phase azeotrope with the isopropanol in the recovery column and some other method of separation will have to be used, as well as having a deleterious effect on the extractive distillation. The ratios shown in Tables II, III and IV are the parts by weight of extractive agent used per part of isopropyl ether-isopropanol-water azeotrope and the two relative volatilities correspond to the two different ratios. For example in Table II, one part of isopropyl ether-isopropanol-water azeotrope with one part of diethylene glycol methyl ether gives a relative volatility of 2.72, 6/5 parts of diethylene glycol methyl ether gives 2.17. One half part of DMFA mixed with one half part of ethylene glycol with one part of isopropyl ether-isopropanol-water azeotrope gives a relative volatility of 3.84, 3/5 parts of DMFA plus 3/5 parts of ethylene glycol gives 3.09. One third parts of DMFA plus ⅓ parts of DMSO plus ⅓ parts of ethylene glycol mixed with one part of isopropyl ether-isopropanol-water azeotrope gives a relative volatility of 5.63, with 2/5 parts, these three give 2.44.

Table IV lists some compounds and combinations of the same components presented in Tables II and III which failed to give relative volatilities above 1.0. This is due to the inability of these compounds or mixtures to negate the isopropyl ether-isopropanol-water azeotrope.

Several of the compounds and mixtures listed in Tables II and III and whose relative volatility had been determined in the vapor-liquid equilibrium still, were then evaluated in a glass perforated plate rectification column possessing 4.5 theoretical plates. The results are listed in Table V. The isopropyl ether-isopropanol-water mixture studied contained 10% isopropyl ether, 85% isopropanol, 5% water. The ternary azeotrope contains 88.0 wt.% isopropyl ether, 7.3 wt.% isopropanol and 4.7 wt.% water. What is remarkable is that pure isopropyl ether comes off as overhead product. In every case the feed or bottoms product contained less than 88% isopropyl ether and in every case the overhead is richer than 88% isopropyl ether. Without extractive distillation agents, the overhead would be the azeotrope, 88% isopropyl ether. This proves that the extractive agent is negating the azeotrope and makes the rectification proceed as if the azeotrope no longer existed and brings the more volatile component, isopropyl ether, out as overhead. It is our belief that this is the first time that this has been reported for this azeotrope.

The data in Table V was obtained in the following manner. The charge designated "blank" was 10% isopropyl ether, 85% isopropanol and 5% water and after 1.5 hours operation in the 4.5 theoretical plate column, the relative volatility of the separation between the isopropyl ether-isopropanol-water azeotrope and isopropanol was 3.28. The remaining data is for the extractive distillation agents designated. Here we have negated the azeotrope and brought out the pure isopropyl ether as overhead. The temperature of the overhead approaches 63° C., the boiling point of pure isopropyl ether at 630 mm. Hg. and the starting material was the isopropyl ether-isopropanol-water azeotrope.

TABLE II

Extractive Distillation Agents Which Are Exceptionally Effective In Separating Isopropyl Ether As Overhead From Isopropanol.

| Compounds | Ratios | | Relative Volatilities | |
|---|---|---|---|---|
| Diethylene glycol methyl ether | 1 | 6/5 | 2.72 | 2.17 |
| Diethylene glycol ethyl ether | " | " | 3.55 | 2.30 |
| Dimethylformamide (DMFA), Ethylene glycol | $(\frac{1}{2})^2$ | $(3/5)^2$ | 3.84 | 3.09 |
| DMFA, Propylene glycol | " | " | 4.36 | 2.59 |
| DMFA, 1,4-Butanediol | " | " | 4.03 | 3.23 |
| DMFA, 1,6-Hexanediol | " | " | 2.70 | 2.35 |
| DMFA, Hexylene glycol | " | " | 2.95 | 1.95 |
| DMFA, Glycerine | " | " | 5.32 | 2.63 |
| DMFA, Diethylene glycol | " | " | 3.50 | 2.83 |
| DMFA, Triethylene glycol | " | " | 2.12 | 2.97 |
| DMFA, Dipropylene glycol | " | " | 4.33 | 2.04 |
| DMFA, Diethylene glycol ethyl ether | " | " | 3.45 | 1.57 |
| DMFA, Ethylene carbonate | " | " | 2.00 | 4.06 |
| Ethylene carbonate, Adiponitrile | " | " | 1.95 | 3.50 |
| Adiponitrile, N,N—Dimethylacetamide | " | " | 2.25 | 2.25 |
| DMFA, 1,2,6-Hexanetriol | " | " | 2.82 | 2.08 |
| DMFA, Dimethylsulfoxide (DMSO), Ethylene glycol | $(\frac{1}{3})^3$ | $(2/5)^3$ | 5.63 | 2.44 |
| DMFA, DMSO, Propylene glycol | " | " | 4.33 | 2.47 |
| DMFA, DMSO, 1,4-Butanediol | " | " | 5.70 | 5.46 |
| DMFA, DMSO, 1,5-Pentanediol | " | " | 3.62 | 4.71 |
| DMFA, DMSO, Hexylene glycol | " | " | 4.36 | 2.76 |
| DMFA, DMSO, 3-Ethyl-1,3-hexanediol | " | " | 2.80 | 2.04 |
| DMFA, DMSO, Glycerine | " | " | 3.15 | 3.43 |
| DMFA, DMSO, Diethylene glycol | " | " | 3.13 | 1.96 |
| DMFA, DMSO, Triethylene glycol | " | " | 5.51 | 3.19 |
| DMFA, DMSO, Dipropylene glycol | " | " | 5.30 | 3.06 |
| DMFA, DMSO, 1,6-Hexanediol | " | " | 5.64 | 5.60 |
| DMFA, DMSO, Ethylene glycol methyl ether | " | " | 2.35 | 2.44 |
| DMFA, DMSO, Ethylene glycol ethyl ether | " | " | 5.95 | 2.60 |
| DMFA, DMSO, Ethylene glycol butyl ether | " | " | 4.14 | 2.77 |

TABLE II-continued

Extractive Distillation Agents Which Are Exceptionally Effective In Separating Isopropyl Ether As Overhead From Isopropanol.

| Compounds | Ratios | | Relative Volatilities | |
|---|---|---|---|---|
| DMFA, DMSO, Ethylene glycol hexyl ether | " | " | 4.25 | 3.26 |
| DMFA, DMSO, Diethylene glycol methyl ether | " | " | 3.24 | 2.47 |
| DMFA, DMSO, Diethylene glycol ethyl ether | " | " | 4.98 | 3.34 |
| DMFA, DMSO, Diethylene glycol diethyl ether | " | " | 4.06 | 4.25 |
| DMFA, DMSO, Dipropylene glycol methyl ether | " | " | 2.89 | 2.37 |
| DMFA, DMSO, Propylene glycol methyl ether | " | " | 4.46 | 1.62 |
| DMFA, DMSO, Ethylene glycol ethyl ether acetate | " | " | 3.09 | 3.38 |
| DMFA, DMSO, Diethylene glycol ethyl ether acetate | " | " | 2.94 | 2.79 |
| DMFA, DMSO, Hexylene glycol diacetate | " | " | 4.21 | 1.77 |
| DMFA, DMSO, Isobornyl acetate | " | " | 2.55 | 5.54 |
| DMFA, DMSO, Propoxypropanol | " | " | 3.22 | 4.41 |
| DMFA, DMSO, Butoxypropanol | " | " | 3.50 | 3.14 |
| DMFA, DMSO, Adiponitrile | " | " | 3.66 | 3.20 |
| DMFA, DMSO, Propylene carbonate | " | " | 2.90 | 4.39 |
| DMFA, DMSO, Tricresyl phosphate | " | " | 2.90 | 4.39 |
| DMFA, Adiponitrile, Ethylene carbonate | " | " | 3.92 | 3.29 |
| Adiponitrile, N,N—Dimethylacetamide, Ethylene carbonate | " | " | 3.08 | 3.29 |

TABLE III

Extractive Distillation Agents Which Are Effective In Separating Isopropyl Ether As Overhead From Isopropanol.

| Compounds | Ratios | | Relative Volatilities | |
|---|---|---|---|---|
| DMFA | 1 | 6/5 | 1.94 | — |
| N,N—Dimethylacetamide | " | " | 0.94 | 1.51 |
| Ethylene glycol hexyl ether | " | " | 2.00 | 1.33 |
| Propylene glycol methyl ether | " | " | 1.72 | 1.35 |
| Diethylene glycol butyl ether | " | " | 1.55 | 1.46 |
| DMFA, Tetraethylene glycol | $(\frac{1}{2})^2$ | $(3/5)^2$ | 2.55 | 1.38 |
| DMFA, 3-chloro-1,2-propanediol | " | " | 2.39 | 1.17 |
| DMFA, Polyethylene glycol 300 | " | " | 2.28 | 2.66 |
| DMFA, Propylene glycol methyl ether | " | " | 2.45 | 1.59 |
| DMFA, N,N—Dimethylacetamide | " | " | 1.08 | 1.02 |
| Diethylene glycol diethyl ether, DiEtglycolEt ether | " | " | 2.01 | 1.60 |
| Diethylene glycol diethyl ether, Propylene glycol ethyl ether | " | " | 1.41 | 1.62 |
| Diethylene glycol butyl ether, DiET glycol Hex ether | " | " | 1.10 | 1.52 |

TABLE IV

Extractive Distillation Agents Which Are Ineffective In Separating Isopropyl Ether From Isopropanol And Water.

| Compound | Ratios | | Relative Volatilities | |
|---|---|---|---|---|
| Ethylene glycol butyl ether | 1 | 6/5 | 0.18 | 0.42 |
| Ethylene glycol hexyl ehter | " | " | 0.48 | 0.41 |
| Diethylene glycol diethyl ether | " | " | 0.29 | 0.29 |
| Diethylene glycol butyl ether | " | " | 0.24 | 0.32 |
| Isobornyl acetate | " | " | 0.26 | 0.32 |
| Ethylene glycol methyl ether, DiEtglycol diEt ether | $(\frac{1}{2})^2$ | $(3/5)^2$ | 0.41 | 0.53 |
| Ethylene glycol methyl ether, Ethylyene glycol Hex ether | " | " | 0.40 | 0.44 |

TABLE IV-continued

Extractive Distillation Agents Which Are Ineffective
In Separating Isopropyl Ether From Isopropanol And Water.

| Compound | Ratios | | Relative Volatilities | |
|---|---|---|---|---|
| Ethylyene glycol butyl ether, Ethylene glcyol hexyl ether | " | " | 0.26 | 0.55 |
| Ethylene glycol Bu ether, DiEt glycol diEt ether | " | " | 0.26 | 0.47 |
| Ethylene glycol hexyl ether, DiEt glycol Me ether | " | " | 0.45 | 0.49 |
| Ethylene glycol hexyl ether, DiEtglycol diEt ether | " | " | 0.36 | 0.46 |
| Diethylene glycol Me ether, Ethylene glycol Hex ether | " | " | 0.32 | 0.35 |
| Diethylene glycol Me ether, DiEt glycol diEt ether | " | " | 0.34 | 0.28 |
| Diethylene glycol Me ether, Isobornyl acetate | " | " | 0.27 | 0.29 |
| Diethylene glycol Bu ether, DiEt glycol diET ether | " | " | 0.36 | 0.18 |
| Diethylene glycol diMe ether, Isophorone | " | " | 0.47 | 0.31 |
| Diethylene glycol diEt ether, Isobornyl acetate | " | " | 0.22 | 0.24 |
| Ethylene glycol methyl ether | 1 | 6/5 | 0.72 | 0.51 |
| Ethylene glycol ethyl ether | " | " | 0.71 | 0.51 |
| Ethylene glycol butyl ether | " | " | 0.64 | 0.42 |
| Diethylene glycol methyl ether | " | " | 0.79 | 0.70 |
| Diethylene glycol dimethyl ether | " | " | 0.42 | 0.62 |
| Diethylene glycol ethyl ether | " | " | 0.79 | 0.69 |
| Propoxypropanol | " | " | 1.06 | 0.52 |
| 2,4-Pentanedione | " | " | 0.85 | 1.21 |
| Isophorone | " | " | 0.52 | 0.64 |
| Ethylene glycol methyl ether, DiEt glycol diMe ether | $(1)^2$ | $(3/5)^2$ | 0.58 | 0.59 |
| Ethylene glycol ethyl ether, DiEt glycol diMe ether | " | " | 0.66 | 0.49 |
| Ethylene glycol ethyl ether, DiEt glycol diEt ether | " | " | 0.51 | 0.59 |
| Ethylene glycol butyl ether, DiEt glycol diMe ether | " | " | 0.83 | 0.40 |
| Ethylene glycol butyl ether, DiEt glycol diEt ether | " | " | 0.77 | 0.69 |
| Ethylene glycol hexyl ether, DiEt glycol diEt ether | " | " | 0.91 | 0.32 |
| Diethylene glycol ethyl ether, Isophorone | " | " | 0.69 | 0.79 |
| Diethylene glycol diEt ether, 2,4-Pentanedione | " | " | 0.50 | 0.55 |
| Diethylene glycol diMe ehter, 2,4-Pentanedione | " | " | 0.45 | 0.57 |
| Isobornyl acetate, 1-Butoxyethoxy-2-propanol | " | " | 0.73 | 0.92 |
| 2,4-Pentanedione, DMFA | $(\frac{1}{2})^2$ | $(3/4)^2$ | 0.69 | 0.89 |
| 2,4-Pentanedione, Isophorone | " | $(6/10)^2$ | 0.57 | 0.49 |
| 2,4-Pentanedione, Isophorone, | $(\frac{1}{2})^3$ | $(2/5)^3$ | 0.81 | 0.87 |

TABLE V

Data From Runs Made In Rectification Column

| Compounds | Overhead Temp. °C. | Phases in Overhead | Relative Volatility |
|---|---|---|---|
| Blank (no agent) | 56.8 | 2 | 3.28* |
| Diethylene glycol diethyl ether | 62.6 | 2 | 3.20* |
| Isobornyl acetate | 66.2 | 2 | 2.10* |
| Dimethylsulfoxide (DMSO) | 63.6 | 1 | 5.99 |
| Propylene glycol | 63.2 | 1 | 4.88 |
| Ethylene glycol | 62.2 | 2 | 5.18 |
| Dimethylformamide (DMFA) | 61.4 | 2 | 4.70 |
| DMSO(R), Diethylene glycol diethyl ether(R) | 63.0 | 2 | 4.40 |
| DMSO(R), DiEt glycol diEt ether(R), DMFA(R) | 61.6 | 2 | 4.74 |
| DMSO(R), DMFA(R) | 62.2 | 2 | 4.19 |
| DMSO(R), DMFA(R), Propylene glycol(R) | 61.8 | 2 | 4.72 |
| DMSO(R), Propylene glycol(R) | 62.6 | 1 | 5.71 |
| DMSO(R), Propylene glycol(R), DiEt glycol diEt ether(R) | 61.8 | 2 | 4.97 |
| DMSO(R), Ethylene glycol(R) | 62.8 | 1 | 5.79 |

Notes:
*did not negate the azeotrope.
(R) agent was reclaimed and reused.
Feed composition was 50 gr. isopropyl ether, 425 gr. isopropanol, 25 gr. water.

The ratios are the parts by weight of extractive agent used per part of isopropyl ether-isopropanol-water azeotrope. The relative volatilities are listed for each of the two ratios employed.

The compounds that are effective as extractive distillation agents when used alone are dimethylformamide, N,N-dimethylacetamide, ethylene glycol hexyl ether, propylene glycol methyl ether, diethylene glycol methyl ether, diethylene glycol ethyl ether and diethylene glycol butyl ether. The compounds that are effective when used in mixtures of two or more components are ethylene glycol, propylene glycol, 1,4-butanediol, 1,5-pentanediol, 1,6-hexanediol, hexylene glycol, diethylene glycol, triethylene glycol, dipropylene glycol, 3-ethyl-1,3-hexanediol, 3-chloro-1,2-propanediol, polyethylene glycol, glycerine, 1,2,6-hexanetriol, ethylene glycol methyl ether, ethylene glycol ethyl ether, ethylene glycol butyl ether, ethylene glycol hexyl ether, propylene glycol methyl ether, propylene glycol ethyl ether, diethylene glycol diethyl ether, hexylene glycol diacetate, ethylene glycol ethyl ether acetate, diethylene glycol ethyl ether acetate, isobornyl acetate, ethylene carbonate, propylene carbonate, propoxypropanol, butoxypropanol, dimethylsulfoxide, adiponitrile, tricresyl phosphate.

The breaking of this azeotrope by extractive distillation is a new concept. One of the first applications of this concept might be the breaking of the ethanol-water azeotrope. J. Schneible, (U.S. Pat. No. 1,469,447) used glycerol; P. V. Smith and C. S. Carlson (U.S. Pat. No. 2,559,519) employed ethoxyethanol and butoxyethanol for this purpose and W. E. Catterall (U.S. Pat. No. 2,591,672) reported gasoline as being effective. These are dehydrations and operate more conventionally as a solvent extraction process rather than an extractive distillation. The closest process to this system is probably the breaking of the ethyl acetate-ethanol-water azeotrope by extractive distillation reported by Berg & Ratanapupech (U.S. Pat. No. 4,379,028, Apr. 5, 1983).

OBJECTIVE OF THE INVENTION

The object of this invention is to provide a process or method of extractive distillation that will enhance the relative volatility of isopropyl ether from isopropanol and water in their separation in a rectification column. It is a further object of this invention to identify suitable extractive distillation agents which will eliminate the isopropyl ether-isopropanol-water azeotrope and make possible the production of pure isopropyl ether and isopropanol by rectification. It is a further object of this invention to identify organic compounds which, in addition to the above constraints, are stable, can be separated from isopropanol and water by rectification with relatively few plates and can be recycled to the extractive distillation column and reused with little decomposition.

SUMMARY OF THE INVENTION

The objects of this invention are provided by a process for separating isopropyl ether from isopropanol and water which entails the use of certain oxygenated, nitrogenous and/or sulfur containing organic compounds as the agent in extractive distillation.

DETAILED DESCRIPTION OF THE INVENTION

We have discovered that certain oxygenated, nitrogenous and/or sulfur containing organic compounds, some individually but principally as mixtures, will effectively negate the isopropyl ether-isopropanol-water azeotrope and permit the separation of pure isopropyl ether from isopropanol and water by rectification when employed as the agent in extractive distillation. Table II lists the compounds, mixtures and approximate proportions that we have found to be exceptionally effective. Table III lists the compounds, mixtures and approximate prpoportions that are successful but do not give quite as high a relative volatility as that obtained from those in Table II. Table IV lists those mixtures which we have found to be unsuccessful. The data in Tables II, III and IV were obtained in a vapor liquid equilibrium still. In each case, the isopropanol and water go to the stillpot with the extractive distillation agent. The designation "R" by the extractive distillation agent means that the same material was recovered and re-used to show its stability in repeated operation. When the isopropanol-water-extractive distillation agent mixture taken from the stillpot is redistilled, isopropanol-water azeotrope comes off at 80.3° C. followed by isopropanol at 82.5° C.

THE USEFULNESS OF THE INVENTION

The usefulness or utility of this invention can be demonstrated by referring to the data presented in Tables II, III and V. All of the successful extractive distillation agents show that isopropyl ether can be removed from its ternary minimum azeotrope with isopropanol and water by means of distillation in a rectification column and that the ease of separation as measured by relative volatility is considerable. Without the extractive distillation agents, no improvement above the azeotrope composition will occur in the rectification column. The data also show that the most attractive agents will operate at a boilup rate low enough to make this a useful and efficient method of recovering high purity isopropyl ether from any mixture with isopropanol and water including the ternary minimum azeotrope. The stability of the compounds used and the boiling point difference is such that complete recovery and recycle is obtainable by a simple distillation and the amount required for make-up is small.

WORKING EXAMPLES

Example 1

The isopropyl ether-isopropanol-water ternary azeotrope is 88% isopropyl ether, 7.3% isopropanol and 4.7% water. Thirty grams of the isopropyl ether-isopropanol-water azeotrope and 30 grams of dimethylsulfoxide (DMSO) were charged to an Othmer type glass vapor-liquid equilibrium still and refluxed for 11 hours. Analysis of the vapor and liquid by gas chromatography gave vapor 99%, isopropyl ether, 1% isopropanol; liquid of 94.7% isopropyl ether, 5.3% isopropanol. This indicates a relative volatility of 5.54. Ten grams of the azeotrope were added and refluxing continued for another nine hours. Analysis indicated a vapor composition of 98.8% isopropyl ether, 1.2% isopropanol, a liquid composition of 93.9% isopropyl ether, 6.1% isopropanol which is a relative volatility of 5.35. The lower concentration of extractive agent gives a lower relative volatility as expected.

Example 2

Thirty grams of the isopropyl ether-isopropanol-water azeotrope, 10 grams of DMSO, 10 grams of dimethylformamide (DMFA) and 10 gms. of diethylene glycol methyl ether were charged to the vapor-liquid equilibrium still and refluxed for four hours. Analysis indicated a vapor composition of 97.7% isopropyl ether, 2.3% isopropanol, a liquid composition of 86.4% isopropyl ether, 13.6% isopropanol which is a relative volatility of 6.68 Ten grams of the azeotrope were added and refluxing continued for another seven hours. Analysis indicated a vapor composition of 97.2% isopropyl ether, 3.8% isopropanol, a liquid composition of 89.7% isopropyl ether, 10.3% isopropanol which is a relative volatility of 4.0.

Example 3

Thirty grams of the isopropyl ether-isopropanol-water azeotrope, 15 grams of DMFA, 10 grams of dimethylsulfoxide (DMSO) and 10 grams of 1,4-butanediol were charged to the vapor-liquid equilibrium still and refluxed for four hours. Analysis indicated a vapor composition of 98.8% isopropyl ether, 1.2% isopropanol, a liquid composition of 93.9% isopropyl ether, 6.1% isopropanol which is a relative volatility of 5.70. Ten grams of the azeotrope were added and refluxing continued for another seven hours. Analysis indicated a vapor composition of 96.5% isopropyl ether, 3.5% isopropanol, a liquid composition of 83.3% isopropyl ether, 16.7% isopropanol which is a relative volatility of 5.46.

Example 4

A glass perforated plate rectification column was calibrated with ethylbenzene and p-xylene which possesses a relative volatility of 1.06 and found to have 4.5 theoretical plates. A solution of 50 grams of isopropyl ether, 425 grams of isopropanol and 25 grams of water was placed in the stillpot and heated. When refluxing began, an extractive agent containing pure dimethylsulfoxide was pumped into the column at a rate of 20 ml/min. The temperature of the extractive agent as it entered the column was 58° C. After establishing the feed rate of the extractive agent, the heat input to the isopropyl ether, isopropanol and water in the stillpot was adjusted to give a total reflux rate of 10–20 ml/min. After one hour of operation, overhead and bottoms samples of approximately two ml. were collected and analysed using gas chromatography. The ratio of isopropyl ether to isopropanol in the overhead was 83.7:1. The ratio of isopropyl ether to isopropanol in the bottoms was 0.05:1. Using these ratios in the Fenske equation, with the number of theoretical plates in the column being 4.5, gave an average relative volatility of 5.20. After 1.5 hours of operation, the overhead and bottoms samples were taken and analysed. The ratio of isopropyl ether to isopropanol in the overhead was 125.6:1; the ratio of isopropyl ether to isopropanol in the bottoms was 0.04:1. This gave an average relative volatility of 5.99. After two hours of total operating time, the overhead and bottoms samples were again taken and analysed. The ratio of isopropyl ether to isopropanol in the overhead was 136:1; the ratio of isopropyl ether to isopropanol in the bottoms was 0.034:1. This gave an average relative volatility of 6.32.

Example 5

A solution of 50 grams of isopropyl ether, 425 grams of isopropanol and 25 grams of water was placed in the stillpot of the same column used in example 4 and heat applied. When refluxing began, an extractive agent comprising 50% DMSO and 50% ethylene glycol was fed into the top of the column at a feed rate of 20 ml/min and a temperature of 58° C. After establishing the feed rate of the extractive agent, the heat input to the isopropyl ether, isopropanol and water in the stillpot was adjusted to give a total reflux rate of 10-20 ml/min. Having established the reflux rate, the column was allowed to operate for two hours. After one hour of steady operation, the overhead and bottoms samples of approximately two ml. were collected and analysed by gas chromatography. The ratio of isopropyl ether to isopropanol in the overhead was 71.5:1. The ratio of isopropyl ether to isopropanol in the bottoms was 0.05:1. Using these ratios in the Fenske equation with the number of theoretical plates of the column being 4.5, gave an average relative volatility of 5.07. After 1.5 hours of steady operation, the ratio of isopropyl ether to isopropanol in the overhead was 81.1; the ratio of isopropyl ether to isopropanol in the bottoms was 0.03:1. This gave an average relative volatility of 5.79. After two hours of total operation, the ratio of isopropyl ether to isopropanol in the overhead was 84:1; the ratio of isopropyl ether to isopropanol in the bottoms was 0.03:1. This gave an average relative volatility of 5.81.

The nature of the present invention having been described, what we wish to claim as new and useful and secure by Letters Patent is:

1. A method for recovering essentially anhydrous isopropyl ether from a mixture of isopropyl ether, isopropanol and water, which comprises distilling a mixture of isopropyl ether, isopropanol and water in a rectification column in the presence of an extractive agent, recovering essentially pure isopropyl ether as overhead and obtaining the extractive agent and isopropanol and water from the stillpot or reboiler, the extractive agent comprises at least dimethylsulfoxide.

2. The method of claim 1 in which the extractive agent comprises a mixture of dimethylsulfoxide and at least one of the group consisting of ethylene glycol, propylene glycol, 1,4-butanediol, 1,5-pentanediol, hexylene glycol, 3-ethyl-1,3-hexanediol, glycerine, diethylene glycol, triethylene glycol, dipropylene glycol, 1,6-hexanediol, tetraethylene glycol, diethylene glycol methyl ether, diethylene glycol ethyl ether, ethylene carbonate, adiponitrile, N,N-dimethylacetamide, 1,2,6-hexanetriol, ethylene glycol methyl ether, ethylene glycol ethyl ether, ethylene glycol butyl ether, ethylene glycol hexyl ether, diethylene glycol diethyl ether, dipropylene glycol methyl ether, propylene glycol methyl ether, ethylene glycol ethyl ether acetate, diethylene glycol ethyl ether acetate, hexylene glycol diacetate, isobornyl acetate, propoxypropanol, butoxypropanol, propylene carbonate, tricresyl phosphate, 3-chloro-1,2-propanediol, polyethylene glycol, propylene glycol ethyl ether and/or diethylene glycol hexyl ether.

* * * * *